United States Patent
Rydell

[11] Patent Number: 5,810,809
[45] Date of Patent: Sep. 22, 1998

[54] ARTHROSCOPIC SHAVER INCORPORATING ELECTROCAUTERY

[75] Inventor: Mark A. Rydell, Golden Valley, Minn.

[73] Assignee: Enhanced Orthopaedic Technologies, Inc., Plymouth, Minn.

[21] Appl. No.: 782,719

[22] Filed: Jan. 13, 1997

[51] Int. Cl.⁶ ................................................. A61B 17/32
[52] U.S. Cl. ........................... 606/49; 606/46; 606/180; 604/22
[58] Field of Search .................. 606/1, 41, 42, 606/45–50, 170, 171, 180; 604/22

[56] References Cited

U.S. PATENT DOCUMENTS

| | | | |
|---|---|---|---|
| 3,945,375 | 3/1976 | Banko | 606/49 |
| 4,640,279 | 2/1987 | Beard. | |
| 4,793,346 | 12/1988 | Mindich. | |
| 4,815,462 | 3/1989 | Clark | 606/180 |
| 4,994,067 | 2/1991 | Summers | 606/170 |
| 5,133,713 | 7/1992 | Huang et al. | 606/46 |
| 5,221,281 | 6/1993 | Klicek. | |
| 5,261,877 | 11/1993 | Fine et al. | 606/180 |
| 5,290,282 | 3/1994 | Casscells. | |
| 5,352,222 | 10/1994 | Rydell. | |
| 5,364,395 | 11/1994 | West, Jr. | 606/46 |
| 5,505,729 | 4/1996 | Rau. | |
| 5,527,331 | 6/1996 | Kreseh et al. . | |

*Primary Examiner*—Michael Peffley
*Attorney, Agent, or Firm*—Haugen and Nikolai, P.A.

[57] ABSTRACT

An arthroscopy instrument for debriding tissue also includes an electrocautery electrode for effecting hemostasis in the surgical site. The drive motor for the debriding instrument is placed remotely from the instrument's handle and provision is made for electrically insulating the handle from the drive motor and associated power supply even though the arthroscopic surgery is taking place under saline.

19 Claims, 7 Drawing Sheets

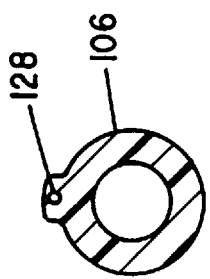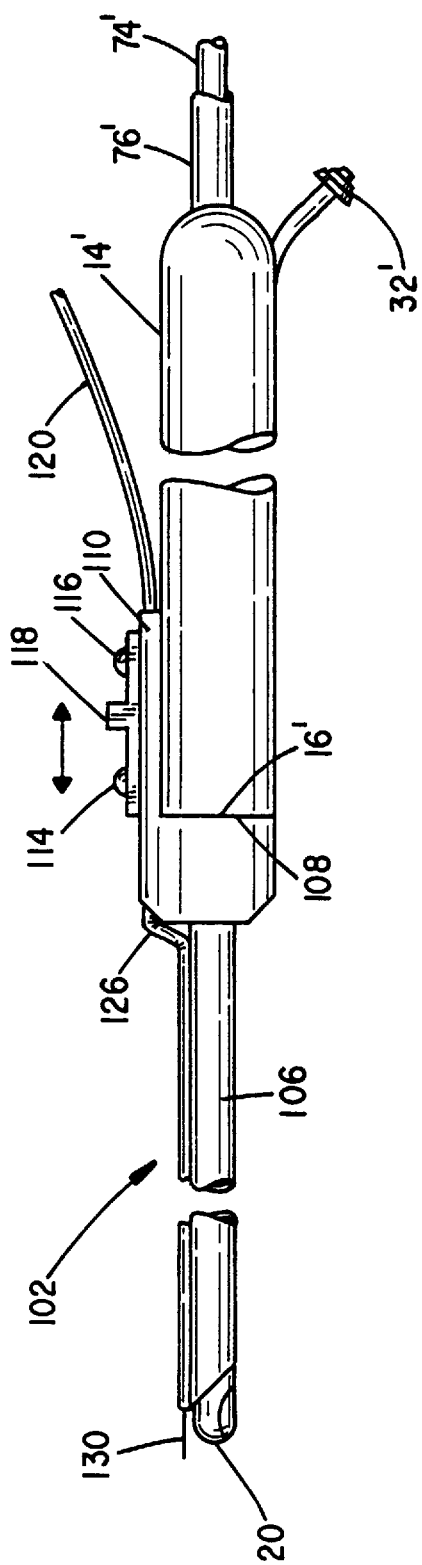

ARTHROSCOPIC SHAVER INCORPORATING ELECTROCAUTERY

BACKGROUND OF THE INVENTION

I. Field of the Invention

This invention relates generally to electrosurgical instruments, and more particularly to an arthroscopy shaver incorporating an electrocautery electrode and constructed such that the hand-held portion of the instrument and the shaver blade drive motor are electrically isolated from the electrocautery voltage.

II. Discussion of the Prior Art

Current arthroscopy shaver technology entails the application of a spinning tube-within-a-tube that concurrently resects tissue while aspirating debris and saline from within the operative site. One such arthroscopy system is the DYONICS® Model EP-1 available from Smith & Nephew Endoscopy, Inc., of Andover, Mass. The shaver instrument comprises a hollow metal handle containing a variable speed electric drive motor whose output shaft is adapted to be coupled to the proximal end of an elongated metal tube whose distal end is beveled and sharpened in the case of a cutter or knurled in the case of a bur. Surrounding the tubular blade is an outer tubular member having a hub at its proximal end adapted to mate with the handle and which remains stationary during use. Formed at the distal end of the outer tubular member is a window-like opening. Provision is made for suction to be applied through the tubular blade assembly to thereby draw tissue through the window-like opening in the outer tube where it is exposed to the cutting surfaces of the inner blade member that is being driven at a high speed by the motor.

One significant problem associated with arthroscopy is the bleeding that occurs when tissue has been resected. Such bleeding is detrimental to the ability to clearly view the progress of the surgery endoscopically. Unless bleeding can be controlled, it is difficult for the orthopaedic surgeon to effectively operate currently, the means to control bleeding include the application of a tourniquet, pressurization of the joint with in-flow media, e.g., saline, inflowing with epinephrine along with saline, and using a separate electrocautery device.

When performing arthroscopic surgery on a knee, a pneumatic tourniquet that inflates around the thigh is used to occlude the flow of blood to the lower leg. While this is effective in bleeding control, there are often patient complications as a result of the lack of blood flow during the procedure, and soft tissue damage as a result of the high-pressure cuff. A tourniquet cannot be used for shoulder arthroscopy, as there is no logical point to apply a cuff between the heart and shoulder joint.

In pressurizing the joint to be operated upon with saline, either through the use of an arthroscopy pump or gravity, the joint is pressurized to a level exceeding systolic (tampanod) blood pressure, such that blood flow is effectively stopped. A potential complication from pressurizing the joint is extravasation of saline into surrounding tissue. This is particularly true in the shoulder, where the surrounding joint capsule is not a well defined constrained structure.

By administering epinephrine, a vasoconstrictor, blood vessels entering the joint are closed off. While relatively effective, epinephrine has the capacity to enter the patient's bloodstream, causing complications that include cardiovascular irregularities, especially tachyarrhythmias.

The last modality commonly used for establishing hemostasis during arthroscopy is electrocautery. When a "bleeder" is exposed, it can be cauterized using an arthroscopic cautery pencil, whereby electrical current is delivered to the vessel through an uninsulated tip electrode. Effective as a means of bleeding control, electrocautery involves the cumbersome removal of one instrument so that the cautery pencil can be inserted. Often, it is difficult for the surgeon to find a bleeder, particularly in the shoulder, and the time that it takes to insert the cautery pencil, find the bleeder and cauterize may exceed the time it takes for the bleeding to completely obliterate the visualization of the surgical site.

From the foregoing, it can be seen that a need exists for an arthroscopic cutter/bur that incorporates an electrocautery electrode at its distal tip such that the same instrument that is used to cut and abride tissue is also used to stem bleeding so that no instrument exchange is required. A problem has remained, however, of how to effectively isolate the physician as well as the drive motor and its power supply therefore from the RF electrosurgery current when it is recognized that the arthroscopic surgery is commonly performed in a field in which saline, a highly conductive fluid, is used to flush tissue debris as the saline is aspirated back through the arthroscopic cutting instrument.

SUMMARY OF THE INVENTION

In accordance with the present invention, there is provided a modified handle assembly capable of accepting a standard, commercially available tube-within-a-tube arthroscopic blade/bur assembly and containing a rigid drive shaft for rotating the inner tubular cutter. Rather than incorporating the drive motor into the handle, the drive shaft is adapted to be driven from a remotely located motor, via a flexible cable drive shaft. Means are provided for applying a monopolar current to the tubular metal blade which is surrounded by an insulating jacket except at the distal end portion of the cutter blade assembly where the window opening is located. The insulating jacket thus effectively limits the size of the electrode area and concentrates the electric field at that location for more effective electrocautery.

The handle of the instrument includes an aspiration lumen that is in fluid communication with a lumen of the inner tubular cutter member for applying suction at the window opening for drawing tissue to be abrided into engagement with the cutter blades. Also mounted on the instrument's handle are electrical push-button switches for selectively applying an RF current from an electrosurgical generator to the electrode surface at the distal end of the instrument.

In accordance with an alternative embodiment, a detachable electrosurgical electrode assembly is adapted to cooperate with the handle of the instrument and the concentrically deployed inner and outer tubes comprising the cutter/bur assembly. Specifically, a double lumen insulating tube is positioned over the outer tubular cutting blade as a sheath. The second lumen contains an elongated wire conductor whose distal end portion is extendable beyond the distal end of the sheath. The double lumen insulating tube includes a head member affixed to its proximal end and that head member is keyed to the handle and includes a thumb slide thereon which is coupled to the elongated wire conductor for advancing and retracting the distal end portion of the wire conductor relative to the distal end of the sheath. The head member also includes a switch housing containing switch contacts for selectively applying electrocautery voltage to the elongated wire conductor.

DESCRIPTION OF THE DRAWINGS

The foregoing features, objects and advantages of the invention will become apparent to those skilled in the art from the following detailed description of a preferred embodiment, especially when considered in light of the following drawings in which like numerals in the several views refer to corresponding parts.

FIG. 9 is a cross-sectional view of the sheath taken along the line 9—9 in FIG. 8; and FIG. 10 is a side elevational view of the arthroscopic cutter/shaver instrument with the electrosurgical attachment affixed thereto.

DESCRIPTION OF THE PREFERRED EMBODIMENT

Figure 1:
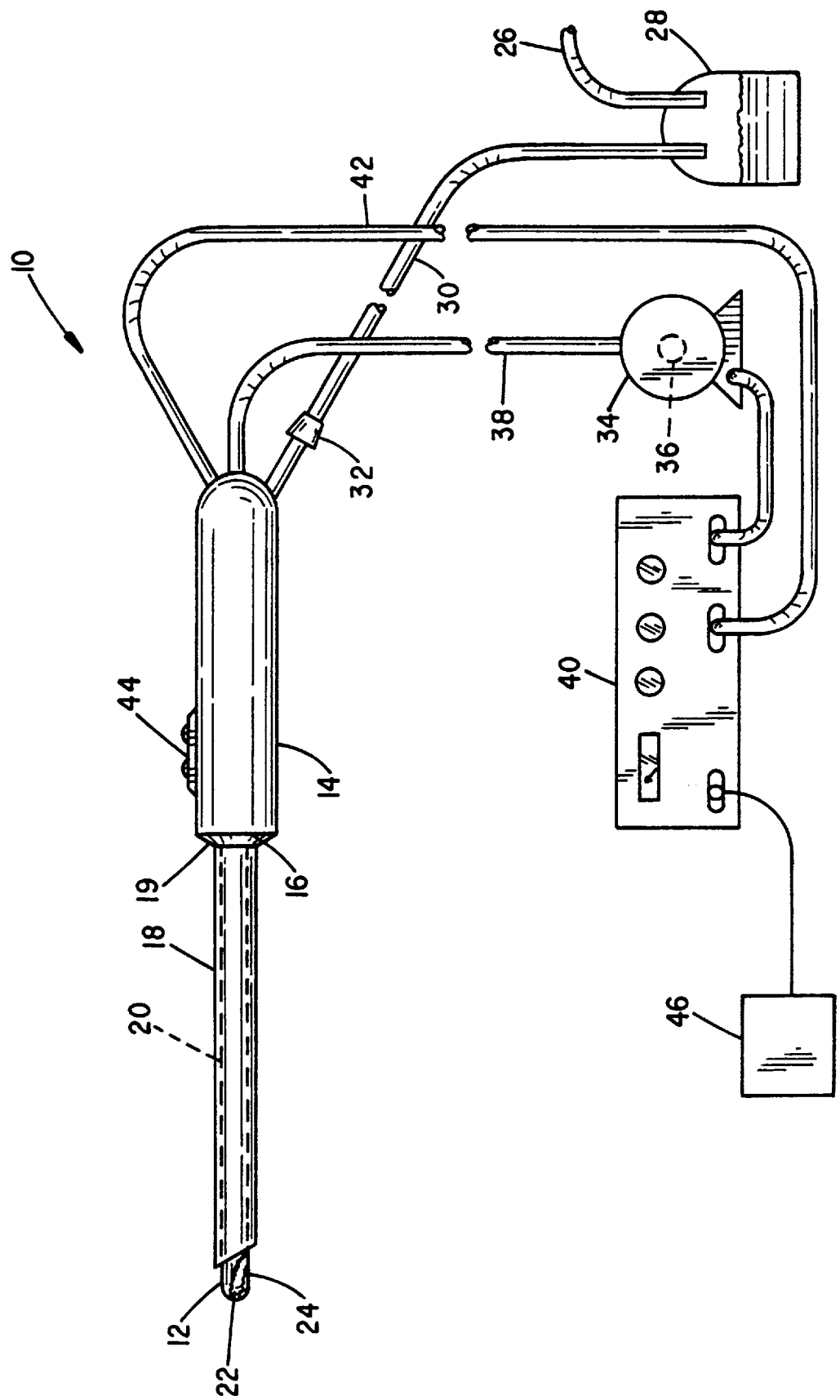
FIG. 1 is a view showing the instrument of the present invention connected to its drive source and power supply.

Referring first to FIG. 1, there is indicated generally by numeral 10 the arthroscopy shaver instrument incorporating an electrocautery electrode surface 12 at a distal end thereof. The instrument itself is seen to comprise an elongated molded plastic handle 14. Projecting outwardly from the distal end 16 of the handle is an insulating sheath 18 that surrounds coaxially disposed inner and outer tubular cutting blades. As will be explained in greater detail hereinbelow, the outermost tubular blade member 20 includes a window-like opening 22 proximate its distal end and rotatably mounted within the central lumen of the outer tube 20 is an inner tube 24. The inner rotatable cutting/debriding blade may take on a number of different cutting head configurations depending upon the nature of the tissue to be resected. Shown here for illustrative purposes only is an inner tube 24 that also has an opening extending through the wall thereof near its distal end and the edges defining the wall are sharpened. As is known in the art, a vacuum is applied, via hose 26, collection bottle 28 and hose 30 to a fitting 32 that is in fluid communication with a lumen extending longitudinally through the handle 14 and leading to the central lumen of the inner tubular cutting blade 24. The suction acts to draw tissue through the window opening 22 so that it is engaged by the spinning cutting edges defining the opening on the inner tubular blade member 24. Associated instruments also include a bur in the form of a hollow ball having a knurled surface, the ball being affixed or formed on the distal end of the inner tubular blade member and the term "cutting blade is intended to include both of these configurations".

Located remotely from the handle 14 of the instrument is a drive motor 34 whose output shaft 36 is connected via a flexible torque transmitting cable 38, similar to a "speedometer" cable, to a rigid drive shaft 70 (FIG. 6) that is journaled for rotation within the handle 14 and coupled to the inner tubular cutter member 24. Thus, the motor 34 and its power supply 40 are electrically and physically isolated from the electrode surface 12. As is known in the art, the speed and mode of operation of the motor 34 may be controlled by a foot switch in a conventional fashion.

Also coupled to the power supply 40 is a cable 42 containing electrical conductors leading to the contacts of a push-button switch assembly 44 mounted on the handle 14. The electrical switches, when actuated, send a signal back to the power supply 40, causing it to apply power to the electrode surface 12 on the distal end of the outer tubular cutter member 20. Indicated by numeral 46 is a return electrode of the type commonly used in monopolar electrosurgery.

Figure 2:
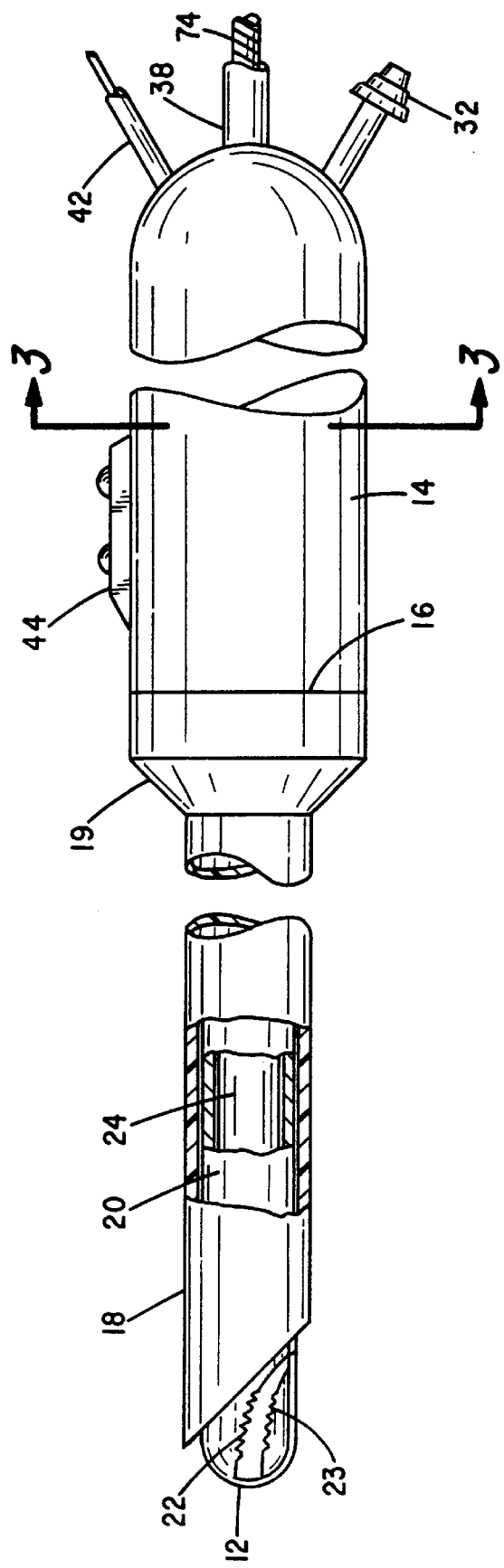
FIG. 2 is a greatly enlarged side elevation of the instrument of FIG. 1.
Figure 3:
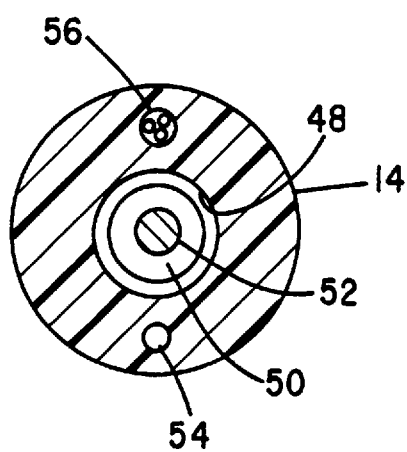
FIG. 3 is a cross-sectional view taken along the line 3—3 in FIG. 2.

Turning next to FIG. 2, the hand-held instrument constructed in accordance with the present invention is illustrated in somewhat enlarged form to better illustrate the relationship between the various parts comprising the assembly. The handle 14 is preferably molded from a suitable, medical-grade plastic, with polysulfone being preferred. As shown by the cross-sectional view of FIG. 3, the handle includes a central lumen 48 and contained within the central lumen are bearings as at 50 for journaling a drive shaft member 52. Also extending longitudinally through the handle 14 is an aspiration lumen 54 leading to the fitting 32 on the exterior of the handle. A further lumen 56 is provided for receiving the electrical cable 42 therein, the wires in which connect to terminals of the push-button switch assembly 44 and to a contact 58 on the hub 19 on the insulating sheath 18 that mates with a contact ring that engages the exterior metal surface of the outer tubular blade member 20.

The outer sheath 18 is plastic, electrically insulating material which coaxially surrounds the outer tubular blade member 20 which, in turn, coaxially surrounds the inner conductive metal tubular cutting member 24. The window opening 22 in the outer tubular blade member and the opening 23 in the inner tubular blade member 24 project distally from the end of the sheath 18.

Figure 6:
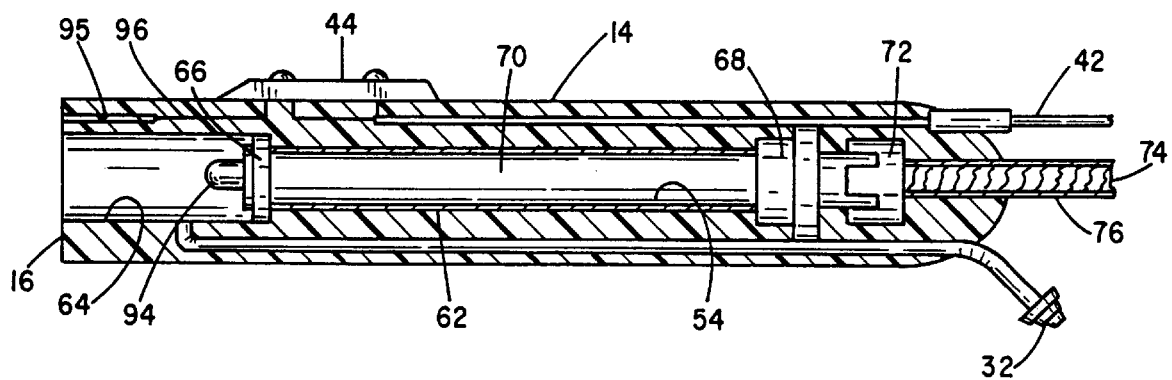
FIG. 6 is a longitudinal, cross-sectional view through the handle of the instrument.

Referring next to the longitudinal cross-sectional view of FIG. 6, the handle 14 is seen to include a longitudinally extending bore 62 which terminates at its distal end 60 in a counterbore 64 of slightly larger diameter than that of the bore 62. Disposed within the counterbore 64 is a first bearing 66 which abuts the annular shoulder defined between the bore 62 and the counterbore 64. A second bearing 68 is likewise disposed within the confines of the handle toward its proximal end. Journaled for rotation in the bearings 66 and 68 is a drive shaft 70. The drive shaft 70 may be fabricated from metal and, in that event, a molded plastic coupler 72 mates with the proximal end of the drive shaft, coupling same to the inner flexible helically wound cable 74 that is adapted to rotate within the confines of the sheath 76. The cable 74 and its sheath 76 comprise the torque transmitting cable 38 referred to earlier. The molded plastic coupler 72 electrically isolates the cable 74 from the drive shaft 70 while still permitting the drive shaft 70 to be driven by the motor 34.

Figure 4:
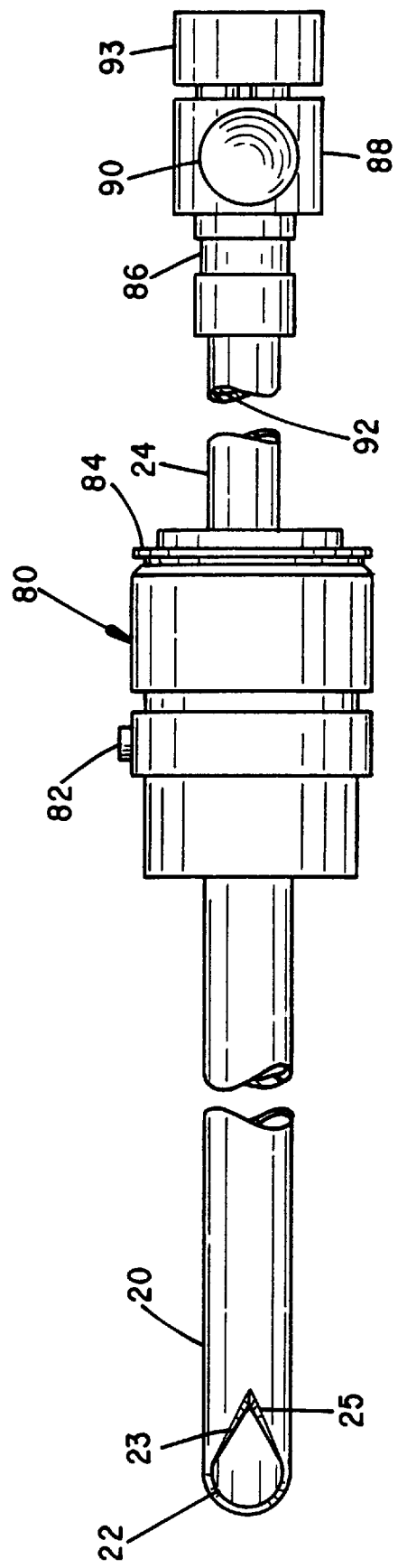
FIG. 4 is a greatly enlarged side elevational view of a conventional, prior art arthroscopic cutting blade assembly usable with the present invention.

FIG. 4 illustrates a typical prior art arthroscopy tube-within-a-tube blade configuration such as is available through Smith & Nephew Endoscopy Inc. It includes an elongated metal tube 20 having a rounded distal end with a tear-drop shaped opening 22 formed therein. The opening is beveled as at 23 and 25 to define sharpened cutting edges. Those edges may be serrated as well. Affixed to the proximal end of the tubular blade 20 is a molded plastic hub 80 having a projecting boss 82 formed thereon for forming a bayonet coupling with a wall of the bore 64 formed in the handle 14.

Fitted into the end of the hub 80 is an elastomeric detent member 84 for operatively engaging an annular notch 86 that is formed on the hub 88 affixed to the proximal end of the inner tubular blade member 24 when the blade member 24 is fully inserted into the outer blade member 20.

The hub 88 also includes a transversely extending bore 90 that is in fluid communication with the central lumen 92 of the tubular blade member 24 and when the coaxially disposed blade assembly is inserted into the socket on the distal end of the handle member defined by the counterbore 64, the aspiration lumen 54 communicates through the opening defined by the bore 90 with the lumen 92 of the inner tubular blade 24. As such, suction will be felt at the window opening 23 (FIG. 2) of the inner blade member 24.

Finally, there is affixed to the proximal end of the hub member 88 a spring-loaded coupler 92 designed to mate with the boss 94 formed on the distal end of the drive shaft 70. Thus, as the drive shaft 70 is being spun by the motor 34, via flexible shaft 74, the inner blade member 24 will rotate at high speed within the lumen of the outer blade member 20.

Figure 5:
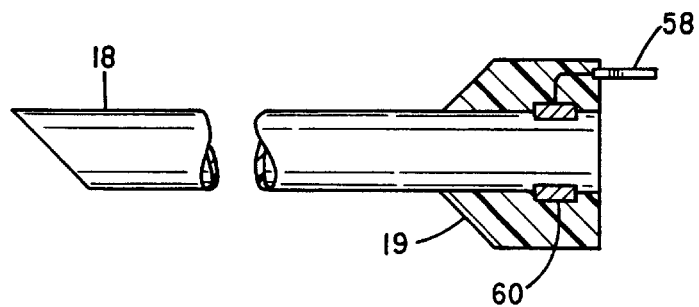
FIG. 5 is a partial, cross-sectional view of the insulating sheath.

Also formed inwardly from the distal end 16 of the handle member 14 is a bore 94 into which is fitted a metal ferrule to which an electrical conductor 96, connected to the push-button switch assembly 44, is attached. Referring to FIG. 5, the ferrule is sized to receive a conductive pin contact 58 when the sheath 18 is assembled over the outer blade member 20 and the hub 19 is made to abut the distal end 16 of the handle 14.

OPERATION

In operation, and with reference to the individual figures, the motor 34 will be electrically connected to the power supply 40 and its output shaft will be coupled via flexible cable drive 38, the insulating coupler 72 and the drive shaft 70 to the inner tubular blade member 24. Likewise, the power supply 40 is connected through electrical leads 42 to push-button switch 44 which, in turn, is connected, via conductor 96 and the pin/socket connector 58/94, to the metal wall of the outer tube 20 when the insulating sheath 18 is fitted thereover. By selecting the appropriate push-button, an appropriate RF voltage will be present on the exposed tip surface 12 of the outer tubular member, allowing monopolar electrocautery between the surface 25 and the body return plate 46. With a vacuum applied to the line 26, a negative pressure will be present at the opening 23 formed in the distal end portion of the inner tubular cutter member 24, causing tissue to be cut to be drawn through the opening 22 in the outer tubular member and exposed to the rapidly rotating blade surfaces of the inner tubular member 23. The tissue is effectively macerated and sucked back through the lumen of the inner tubular member and the lumen 54 in the handle back to the collection jaw 28, via tubing 30.

In the event that the tissue debriding results in a "bleeder", the surgeon may quickly position the exposed electrode surface 12 projecting from the sheath on the bleeder and depress the push-button switch 44 to thereby cauterize the bleeding blood vessel, creating hemostasis. There is no need to remove the instrument from the joint being operated upon, or to insert a separate electrocautery pencil in order to continue the operation.

Even though the surgical procedure may take place in a saline-rich environment, because the handle member 14 of the instrument is plastic and because the drive shaft 70 is electrically insulated from the drive motor, the high frequency electrosurgical current, when being applied by the instrument cannot reach the surgeon nor can it potentially damage the electronic circuitry comprising the power supply 40.

ALTERNATIVE EMBODIMENT

Figure 7:
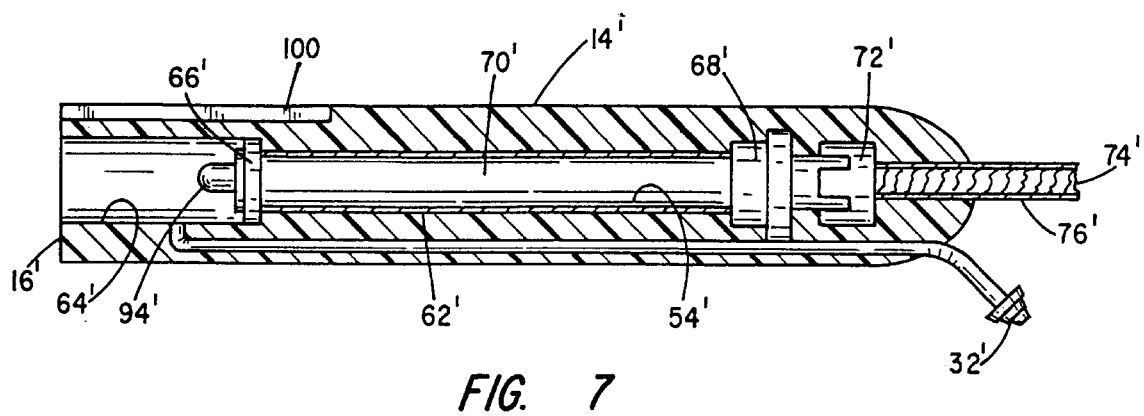
FIG. 7 is a longitudinal, cross-sectional view through the handle of an alternative embodiment of the instrument.

FIGS. 7–10 illustrate an alternative embodiment of an arthroscopic cutter/shaver incorporating an electrocautery electrode. FIG. 7 is a longitudinal cross-sectional view through the handle portion of the instrument and like the previous embodiment, includes an elongated molded plastic handle 14' in which is installed bearings 66' and 68' for journaling a drive shaft 70'. Again, the drive shaft 70' is driven at a variable speed by a motor via a flexible drive cable 74' and a coupler 72'. The flexible cable 74' is contained within a protective sheath 76'.

The handle 14' also includes an aspiration lumen 54' leading to a counterbore 64' extending inwardly from the distal end 16' of the handle. The aspiration lumen 54' terminates in a tubular fitting 32' adapted to mate with further tubing (not shown) leading to a vacuum source.

The counterbore 64' comprises a socket for receiving a prior art cutter blade like that shown in FIG. 4 which has already been described.

The handle member 14' includes a key-way groove 100 formed in the outer surface thereof near the distal end 16' thereof. This key-way provides registration for the electrosurgical attachment indicated generally by numeral 102 in FIG. 8.

The electrosurgical attachment 102 comprises a molded plastic head member 104 supporting an elongated, generally rigid, insulating tube or sheath 106 of a predetermined length that extends in the distal direction. The head member 104 includes a bore 107, allowing the head member to slip over the distal end of the arthroscopic cutting blade and advanced proximally until the edge 108 of the head member 104 abuts the distal end 16' of the handle member 14' as shown in FIG. 10.

Extending in the proximal direction from the edge 108 of the head member 104 is an integrally molded switch housing 110 that is adapted to fit into the key-way 100 on the handle when the two parts are properly mated as illustrated in FIG. 10. The switch housing 110 (FIG. 8) is broken away to show a membrane switch 112 within the housing and having a pair of contacts cooperating with the push buttons 114 and 116 mounted on a thumb slide member 118. Individual wires in the multiconductor cord 120 are appropriately connected to the membrane switch and to a plug 122 that is adapted to mate with an electrosurgical generator.

Figure 8:
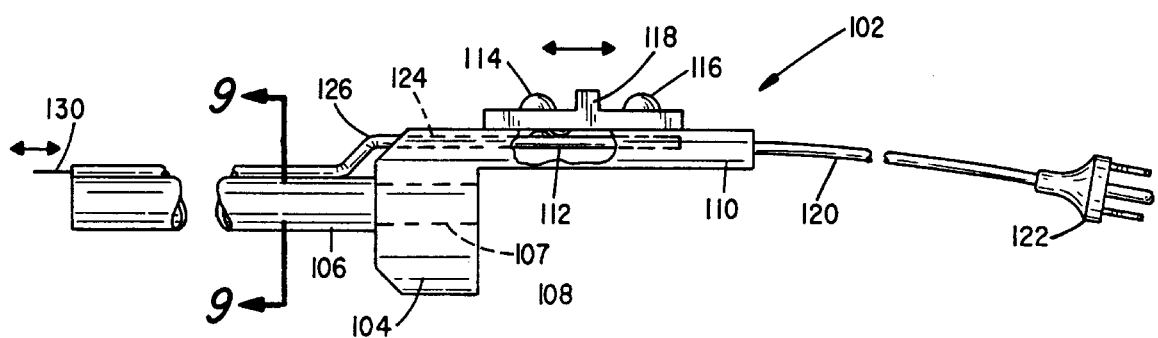
FIG. 8 is a side elevational view of an electrosurgical attachment for the handle of FIG. 7.

Extending from the switch housing 110 is a bore 124 into which is fitted a tubular coupling 126 leading to a second lumen 128 of the sheath 106 (see FIG. 9). Appropriately affixed to the thumb slide 118 and wired to the switches is an elongated flexible wire monopolar electrode 130 that extends through the second lumen 128. The wire electrode 130 is of a length such that when the thumb slide 118 is pushed in the distal direction, a portion of the electrode 130 will extend outwardly beyond the distal end of the tubular sheath 106 as illustrated in FIG. 8. When the thumb slide 118 is pushed in the proximal direction, the electrode 130 becomes fully retracted into the sheath 106.

As is apparent from the foregoing explanation, the electrosurgical attachment 102 is entirely self-contained and designed to slip over the cutter/shaver tube of a prior art arthroscopic blade assembly. The slide 118 supports two push buttons 114 and 116. When the "cut" push button 114 is depressed, a signal is sent back over the cord 120 to the electrosurgical generator 40 (FIG. 1) which responds by applying an appropriate RF voltage, via a conductor in the cord 120, to the electrode wire 130 for effecting RF cutting of tissue. When the push button 116 is depressed, the membrane switch 112 causes a signal to be applied to the electrosurgical generator which then responds by applying an appropriate RF voltage to the wire electrode 130 to cause electrocoagulation. The wire electrode 130 is preferably covered with a dielectric coating, for example, Teflon® heat shrink to limit contact with saline during surgery to the very distal tip portion of the electrode.

As shown in FIG. 9, the sheath 106 is preferably a double-lumen extrusion. The large central lumen is dimensioned so as to provide a light slip fit over the shaver tube 20, and the smaller lumen 128 has a light slip fit around the flexible electrode wire 130. The key-way 100 formed on the handle member 14' is such that when the electrosurgical assembly 102 is installed on the handle, the beveled end of the sheath is in a proper relationship to expose the window opening in the shaver blade.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. In an arthroscopic shaver of the type including a handle for supporting an outer, stationary, elongated, tubular metal cutting blade and an inner, rotatable, elongated, tubular, metal cutting blade, where the outer tubular metal blade includes a window opening proximate a distal end thereof, the handle including an aspiration lumen adapted to be connected to a vacuum source and in fluid communication with a lumen of the inner tubular cutting blade, and motor means for rotating the inner tubular metal cutting blade, the improvement comprising:

(a) means for defining an electrode surface proximate the distal end of the outer tubular cutting blade;

(b) means for applying an electrical cautery voltage to said electrode surface; and (c) flexible drive shaft means for coupling the motor means to the rotatable cutting blade and for electrically isolating the electrocautery voltage from the motor means.

2. The arthroscopic shaver as in claim 1 wherein the means for defining the electrode surface comprises:

(a) an elongated, tubular sheath disposed coaxially relative to the outer tubular metal cutting blade, the sheath covering all but a predetermined area proximate the distal end of the outer tubular cutting blade.

3. The arthroscopic shaver as in claim 1 wherein the motor means for rotating the inner tubular metal cutting blade is located remote from the handle.

4. The arthroscopic shaver as in claim 3 wherein the handle includes a rigid rotatable drive shaft journaled therein, one end of the rigid drive shaft adapted to engage a proximal end of the inner tubular metal cutting blade, the other end of the rigid drive shaft being coupled to the motor means by said flexible drive shaft means.

5. The arthroscopic shaver as in claim 4 wherein the handle is an insulating plastic material.

6. The arthroscopic shaver as in claim 5 wherein said other end of the drive shaft is connected to the flexible drive shaft means by an insulating coupler.

7. The arthroscopic shaver as in claim 2 and further including at least one control switch mounted on the handle for selectively connecting the electrode surface to a source of electrocautery voltage.

8. The arthroscopic shaver as in claim 1 wherein the means for defining an electrode surface proximate the distal end of the outer tubular cutting blade comprises a sheath member having a proximal and a distal end and first and second lumens extending therebetween, the first lumen for containing the outer tubular metal cutting blade and the second lumen for containing an elongated wire conductor with a distal end portion of the wire conductor extendable beyond the distal end of the sheath.

9. The arthroscopic shaver as in claim 8 wherein all but a distal end portion of the elongated wire conductor is covered with an electrically insulating material.

10. The arthroscopic shaver as in claim 8 and further including a head member affixed to the proximal end of the sheath, the head member being keyed to the handle and including a thumb slide member thereon, the thumb slide member being coupled to the elongated wire conductor for advancing and retracting the distal end portion of the wire conductor relative to the distal end of the sheath.

11. The arthroscopic shaver as in claim 10 wherein the head member includes a switch housing containing a switch contact and the thumb slide member includes a push-button for actuating the switch contacts.

12. The arthroscopic shaver as in claim 10 wherein the means for applying an electrocautery voltage to the electrode surface comprises an elongated multiconductor cord having a first terminal for mating with an electrosurgical generator and a second terminal connected to the elongated wire conductor.

13. An arthroscopic shaver incorporating an electrocautery electrode comprising:

(a) a rigid, elongated, tubular handle member having a plurality of lumens extending longitudinally therein;

(b) a drive shaft journaled by bearing means within a first of said plurality of lumens;

(c) a cutter assembly comprising (i) an outer tube having a proximal end, a distal end and a lumen extending therebetween, the outer tube having an opening in a side wall thereof proximal said distal end of said outer tube leading to the lumen of the outer tube and a first hub affixed to the proximal end of the outer tube, (ii) a generally rigid inner tube coaxially disposed and rotatable within the lumen of the outer tube, the inner tube having a cutting element formed thereon proximal a distal end and cooperating with the opening in the side wall of the outer tube, the inner tube including a second hub affixed to a proximate end thereof and journaled to rotate within the first hub on the outer tube;

(d) coupling means on the drive shaft for mating with the second hub when said cutter assembly is inserted into said first of said plurality of lumens;

(e) a tubular insulative sheath coaxially disposed about the outer tube, and having a length dimension less than that of the outer tube to leave the opening unobstructed;

(f) means for applying an electrocautery voltage to the outer tube; and (g) motor means located remote from the tubular handle and coupled to the drive shaft for driving the drive shaft, the motor means being electrically isolated from the electrocautery voltage.

14. The arthroscopic shaver as in claim 13 and further including means coupled to a second of said plurality of lumens in the handle for applying a vacuum to a lumen of the inner tube for drawing tissue to be cut into the opening of the outer tube.

15. In an arthroscopic shaver of the type including a handle for supporting an outer, stationary, elongated, tubular metal cutting blade and an inner, rotatable, elongated, tubular, metal cutting blade, where the outer tubular metal blade includes a window opening proximate a distal end thereof, the handle including an aspiration lumen adapted to be connected to a vacuum source and in fluid communication with a lumen of the inner tubular cutting blade, and motor means for rotating the inner tubular metal cutting blade, the improvement comprising:

(a) means for defining an electrode surface proximate the distal end of the outer tubular cutting blade, that comprises a sheath member having a proximal and a distal end and first and second lumens extending therebetween, the first lumen for containing the outer tubular metal cutting blade and the second lumen for containing an elongated wire conductor with a distal end portion of the wire conductor extendable beyond the distal end of the sheath; and (b) means for applying an electrical cautery voltage to said elongated wire conductor.

16. The arthroscopic shaver as in claim 15 wherein all but a distal end portion of the elongated wire conductor is covered with an electrically insulating material.

17. The arthroscopic shaver as in claim 15 and further including a head member affixed to the proximal end of the sheath, the head member being keyed to the handle and including a thumb slide member thereon, the thumb slide member being coupled to the elongated wire conductor for advancing and retracting the distal end portion of the wire conductor relative to the distal end of the sheath.

18. The arthroscopic shaver as in claim 17 wherein the head member includes a switch housing containing a switch contact and the thumb slide member includes a push-button for actuating the switch contacts.

19. The arthroscopic shaver as in claim 17 wherein the means for applying an electrocautery voltage to the electrode surface comprises an elongated multi-conductor cord having a first terminal for mating with an electrosurgical generator and a second terminal connected to the elongated wire conductor.

* * * * *